United States Patent

Bridges

[11] Patent Number: 5,983,142
[45] Date of Patent: Nov. 9, 1999

[54] TEMPORARY PACING WIRE FOR USE IN CARDIAC SURGERY

[75] Inventor: Charles R. Bridges, Villanova, Pa.

[73] Assignee: The Trustees of the University of Pennsylvania, Philadelphia, Pa.

[21] Appl. No.: 08/995,223

[22] Filed: Dec. 19, 1997

[51] Int. Cl.⁶ ..................................................... A61N 1/05
[52] U.S. Cl. ............................................................. 607/119
[58] Field of Search ................................... 607/117, 122, 607/132

[56] References Cited

U.S. PATENT DOCUMENTS 4,214,594  7/1980  Little ........................................ 607/122
5,792,217  8/1998  Camps et al. ............................ 607/132

*Primary Examiner*—William E. Kamm
*Assistant Examiner*—George R. Evanisko

*Attorney, Agent, or Firm*—Woodcock Washburn Kurtz Mackiewicz & Norris LLP

[57] ABSTRACT

A pacing wire that eliminates the risk of cardiac tamponade when the wires are pulled through the heart muscle for removal by providing a "slip joint" within the pacemaker wire by having one half of the wire fit snugly into the other half while covering the joint with overlapping insulation to provide a water tight seal to prevent risk of short circuit. When the pacing wire is removed, the insulation permits the two component halves to "slip" relative to each other. When the wire is removed, the force applied to the wire at the skin is transferred to the subcutaneous tissue by a "winged insulation umbrella" which prevents motion of the portion of the wire left attached to the heart and transfers the pulling force to the chest wall. Consequently, there is zero net force on the heart where the bare wire is in contact with the heart, leaving this portion of the wire stationary and eliminating risk of damage to the heart muscle.

1 Claim, 1 Drawing Sheet

TEMPORARY PACING WIRE FOR USE IN CARDIAC SURGERY

BACKGROUND OF THE INVENTION

1. Field of the Invention

The present invention relates to a novel pacing wire for use in cardiac surgery, and in particular, to a pacing wire having a slip-joint to facilitate safe and easy removal of the temporary pacing wire upon the patient's post-operative recovery.

2. Description of the Prior Art

After open heart surgery, one or two pairs of temporary pacing wires are typically placed onto the myocardium of the patient and brought out through the patient's chest wall and skin using a Keith needle. Typically, the pacing wires are then sutured to the patient's skin, and the Keith needle is snapped off to allow connection of the pacing wires to a pacemaker. This permits treatment of transient heart block which commonly occurs after open heart surgery. However, the sutures and the pacing wires must then be removed (pulled out through the heart muscle) on the third or fourth postoperative day. The primary complication associated with the removal of the pacing wires is a small incidence of cardiac tamponade, or tear in the heart muscle. The complication is typically manifested in only about 1% of the patients, but the tear to the heart muscle in those cases can be fatal.

FIG. 1 illustrates a standard pacing wire 1 (State of the Art Medical, model M-24). The standard pacing wire 1 (typically 5 cm length) of FIG. 1 is inserted into the myocardium using needle 2 and is insulated by an insulated wire (typically 40 cm length) through the chest wall to outside the patient's body. Once the pacing wire 1 is inserted into the myocardium, the Keith needle 4 is snapped off at snap off point 5, connected to a pacemaker, and sutured to the patient's skin. The pacing wire 1 is removed (pulled) from the heart by pulling the pacing wire 1 at the snap off point 5 at the skin, and the pulling force is directly transmitted to the heart at the bare wire end 1. As just noted, this force and the mechanical energy associated with pulling the bare end of the wire through the heart muscle can result in bleeding, tamponade, and in rare cases, death.

As a result, some surgeons simply cut the wire at the skin to avoid the risk of the infrequent, but potentially devastating complication of cardiac tamponade. Unfortunately, cutting the pacing wire at a point flush with the patient's skin surface is uncomfortable for the patient and leads to a greater risk of infection.

An improved temporary pacing wire is desired which overcomes these difficulties.

SUMMARY OF THE INVENTION

A technique which addresses the above-mentioned needs in the art is described herein. In accordance with the invention, a novel pacing wire is provided that will eliminate the risk of cardiac tamponade when the wires are pulled through the heart muscle for removal. The novel pacing wire of the invention is designed to include a "slip joint" within the pacemaker wire by having one half of the wire fit snugly into the other half while covering the joint with overlapping insulation to provide a water tight seal to prevent risk of short circuit. When the pacing wire is removed, the insulation permits the two component halves to "slip" relative to each other. When the wire is removed, the force applied to the wire at the skin is transferred to the subcutaneous tissue by a "winged insulation umbrella" which prevents motion of the portion of the wire left attached to the heart and transfers the pulling force to the chest wall. Consequently, there is zero net force on the heart where the bare wire is in contact with the heart, leaving this portion of the wire stationary and eliminating risk of damage to the heart muscle.

BRIEF DESCRIPTION OF THE DRAWINGS

The above-mentioned and other objects and advantages of the invention will become more apparent to those skilled in the art from the following detailed description of the invention with reference to the attached drawings, of which.

DETAILED DESCRIPTION OF THE PRESENTLY PREFERRED EMBODIMENTS

Figure 1:
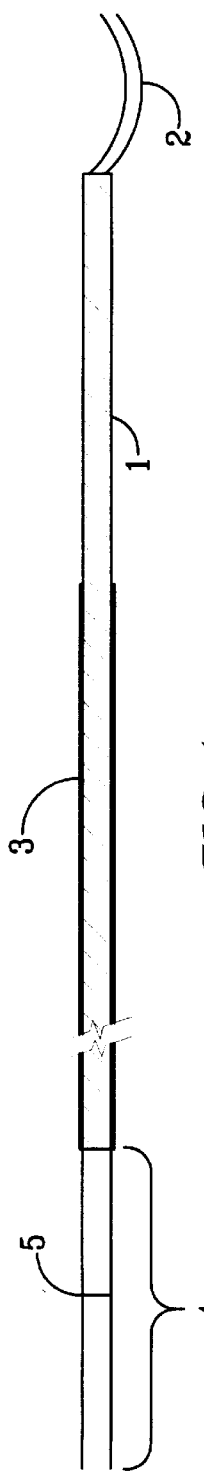
FIG. 1 illustrates a prior art one-piece temporary pacing wire.

A technique which meets the above-mentioned objects and provides other beneficial features in accordance with the presently preferred exemplary embodiment of the invention will be described below with reference to FIG. 2, wherein like reference numerals correspond to like elements in FIG. 1. Those skilled in the art will readily appreciate that the description given herein with respect to those figures is for explanatory purposes only and is not intended in any way to limit the scope of the invention. All questions regarding the scope of the invention should be resolved by referring to the appended claims.

Figure 2:
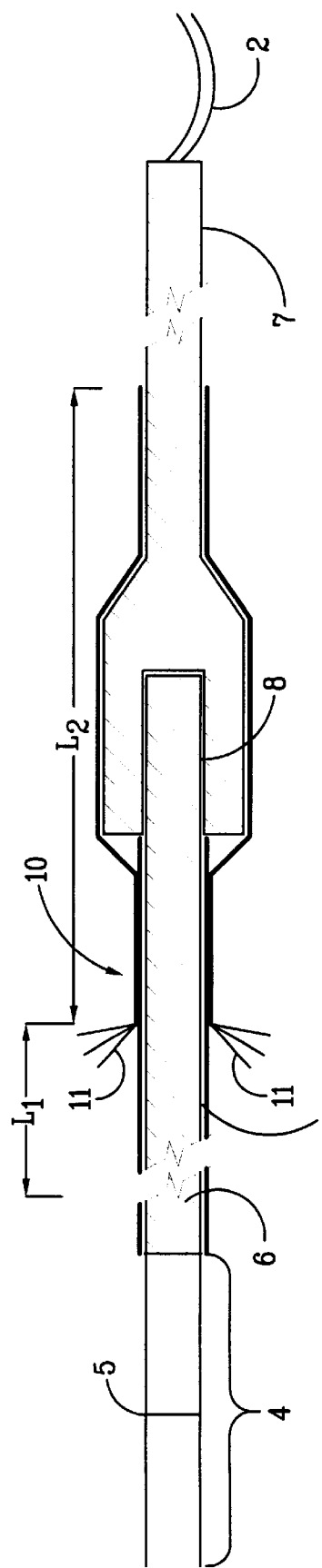
FIG. 2 illustrates a temporary pacing wire in accordance with the invention.

FIG. 2 illustrates a preferred embodiment of the temporary pacing wire of the invention. As illustrated, the single pacing wire 1 of FIG. 1 is replaced by two wire portions 6 and 7 which fit snugly together at contact point 8 to provide a low resistance electrical contact. Overlapping wire insulation sheaths 9 and 10 prevent short circuits and provides a water tight seal around contact point 8. The overlapping wire insulation 9 and 10 have lengths $L_1$ and $L_2$, respectively, which typically have a total (overlapping) length of approximately 40 cm. In accordance with the invention, wire insulation 10 includes a winged insulation umbrella 11 which contacts the inside of the chest wall when a pulling force is applied to the end of the pacing wire outside of the patient (left end of FIG. 2).

In accordance with the invention, the separation point for the wire is at contact point 8, which remains inside the patient's chest wall, rather than flush with the patient's skin. This reduces the risk of infection since the pacing wire 7 remains sterile beneath the chest wall musculature. The bare section of wire portion 7 remains within the patient's myocardium. Also, since the winged insulation umbrella 11 transfers the pulling force to the chest wall, no pulling force is applied to the portion of the pacing wire 7 inserted into the myocardium. Since a significant amount of pulling force can be absorbed by the chest wall, the wires 6 and 7 may be connected tightly enough at contact point 8 to prevent the wires 6 and 7 from coming apart prematurely. In fact, the pacing wire of the invention can absorb an even larger pulling force than conventional pacer wires without becoming dislodged.

Thus, not only is there no risk of damage to the myocardium with the invention, but also there is a decreased risk of dislodgement compared to prior art devices. Specifically, the invention is designed such that the frictional force between the wire portions 6 and is greater than the frictional force typically holding the bare portion of the wire in the myocardium. As a result, an external force which would dislodge a conventional wire from the myocardium (and possibly damage the heart) will fail to separate wire portions 6 and 7.

It will be appreciated by those skilled in the art that the foregoing has set forth the presently preferred embodiment of the invention but that numerous alternative embodiments are possible without departing from the novel teachings of the invention. Accordingly, all such modifications are intended to be included within the scope of the appended claims.

I claim:

1. A pacing wire for use with a pacemaker and for insertion into the myocardium of a patient, said pacing wire comprising:

a first wire portion for insertion into the myocardium of the patient;

a second wire portion having a proximal end and a distal end, said proximal end of said second wire portion being adapted to extend out of the patient's chest wall for connection to said pacemaker, and said distal end of said second wire portion connecting to said first wire portion and forming a contact point at the connection;

a first insulation sheath surrounding a portion of said first wire portion, said first insulation sheath including a winged portion at one end thereof which is adapted to abut an inside portion of the patient's chest wall when said first wire portion is inserted into the myocardium;

a second insulation sheath surrounding a portion of said second wire portion; and a slip joint comprising said first sheath overlapping said second sheath, said slip joint snugly connecting the distal end of said second wire portion to said first wire portion at said contact point and providing a substantially watertight seal about said contact point, whereby a pulling force applied to said proximal end of said second wire portion substantially transfers said pulling force to said inside portion of the patient's chest wall via said slip joint and said winged portion.

* * * * *